United States Patent [19]
Choi

[11] Patent Number: 5,880,303
[45] Date of Patent: Mar. 9, 1999

[54] AMIDOALANE PRECURSORS FOR CHEMICAL VAPOR DEPOSITION OF ALUMINUM

[76] Inventor: Hyungsoo Choi, 2406 Boudreau Dr., Urbana, Ill. 61801

[21] Appl. No.: 943,330

[22] Filed: Oct. 3, 1997

[30]    Foreign Application Priority Data

Jul. 28, 1997 [KR]   Rep. of Korea ...................... 97-35510

[51] Int. Cl.$^6$ ....................................................... C07F 5/06
[52] U.S. Cl. ............................................. 556/176; 556/27
[58] Field of Search ....................................... 556/27, 176

[56]              References Cited

U.S. PATENT DOCUMENTS

| | | | |
|---|---|---|---|
| 3,375,129 | 3/1968 | Curley et al. ......................... | 117/107.2 |
| 5,191,099 | 3/1993 | Gladfelter et al. ........................ | 556/27 |

OTHER PUBLICATIONS

Atwood et al., J. Chem. Soc., Chem. Commun., No. 1, pp. 73–74 1994.

A. Malazgirt et al., "Production of Aluminum and Aluminum Coatings by Thermal Decomposition of Aluminum Alkyls", *Metallurgical transactions B* 11B(1980):225–232.

M. L. Green et al., "Aluminum Films Prepared By Metal–Organic Low Pressure Chemical Vapor Deposition", *Thin Solid Films*, 114(1984):367–377.

Brian E. Bent et al., "Surface Organometallic Chemistry in the Chemical Vapor Deposition of Aluminum Films Using Triisobutylaluminum: β–Hybrid and β–Alkyl Elimination Reactions of Surface Alkyl Intermediates", *J. Am. Chem. Soc.*, 111(1989):1634–1644.

Kurt W. Egger, "Kinetics of the Intramolecular Four–Center Elimination of Isobutylene from Triisobutylaluminum in the Gas Phase", *J. Am. Chem. Soc.*, 91(11):2867–2871, May 21, 1969.

R. A. Levy et al., "Low Pressure Chemical Vapor Deposition of Tungsten and Aluminum for VSLI Applications", *Journal Electrochemical Society*, 134(2):37C–49C, Feb. 1987.

R. Bhat et al., "The Growth and Characterization of AlGaAs Using Dimethyl Aluminum Hydride", *J. Crystal Growth*, 77(1986):7–10.

A. C. Jones et al., "Growth of $Al_xGa_{1-x}As$ By MOVPE Using Alternative Alkyaluminum Precursors", *J. Crystal Growth*, 100(1990):395–404.

Wayne L. Gladfelter et al., "Trimethylamine Complexes Of Alane As Precursors For The Low–Pressure Chemical Vapor Deposition Of Aluminum", *Chemistry of Materials*, 1(1989):339–343.

John K. Ruff et al., "The Amine Complexes of Aluminum Hydride", *J. Am. Chem. Soc.*, 82(1960):2141–2144.

Michael G. Simmonds et al., "Detection Of Aluminum Particles During The Chemical Vapor Deposition Of Aluminum Films Using Tertiaryamine Complexes Of Alane ($AlH_3$)", *J. Vac. Sci. Technol.* A9(5), 1991.

*Primary Examiner*—Porfirio Nazario-Gonzalez
*Attorney, Agent, or Firm*—Burns, Doane, Swecker & Mathis, L.L.P.

[57]              ABSTRACT

This invention provides volatile, intramolecularly coordinated amido/amine alane complexes, $H_2Al\{(R^1)(R^2)NC_2H_4NR^3\}$, wherein $R^1$, $R^2$ and $R^3$ are each independently H or $C_1$–$C_3$ alkyl. These aluminum complexes show extremely high thermal stability and deposit high-quality aluminum films at low temperatures. They are capable of selectively depositing aluminum films on metallic or other electrically conductive substrates with wide process window.

9 Claims, 1 Drawing Sheet

AMIDOALANE PRECURSORS FOR CHEMICAL VAPOR DEPOSITION OF ALUMINUM

BACKGROUND OF THE INVENTION

The present invention relates to the synthesis and use of new aluminum compounds as precursors for chemical vapor deposition (CVD) to obtain high-quality aluminum films. More particularly, the present invention relates to new precursors for chemical vapor deposition of aluminum, which are non-pyrophoric and stable in the gas phase at elevated temperatures to maintain their molecular integrity, and use thereof.

Chemical vapor deposition of aluminum films has attracted much attention as conventional deposition techniques such as sputtering are expected to be problematic for processing ultra large scale integration (ULSI) devices in the microelectronics industry. However, CVD method requires organoaluminum precursors which are volatilized and decomposed to produce aluminum films.

Triisobutylaluminum (TIBA) is one of the organoaluminum precursors which has received the most attention among the trialkyl aluminum compounds as CVD precursors because of its ability to deposit high-purity aluminum films (A. Malazgirt et al., Metallugical Transactions B 1980, vol. 11B, 225; M. A. Green et al., Thin Solid Films 1984, vol. 114, 367; and B. E. Bent et al., J. Am. Chem. Soc. 1989, vol. 111, 1634). However, TIBA has a tendency to decompose to the less volatile diisobutylaluminum hydride in the gas phase (K. W. Egger, J. Am. Chem. Soc. 1969, vol. 91, 2867) and gives aluminum films of poor reflective properties (R. A. Levy et al., J. Electrochem. Soc. 1987, vol. 134, 37C). Dimethylaluminum hydride (DMAH) has been reported to be a substantial improvement over TIBA or other alkyl aluminum complexes (R. Bhat et al., J. Cryst. Growth 1986, 77, 7), but a later study showed that the levels of carbon contamination in the $Al_xGa_{1-x}$ As layers deposited from DMAH were identical to those obtained from trimethylaluminum (A. C. Jones et al., J. Cryst. Growth 1990, 100, 395).

Donor-acceptor complexes of alane ($AliH_3$) such as trihydrido(trialkylamine)aluminum (D. R. Carley et al., U.S. Pat. No. , 3,375,129) have been reported to be used for aluminum plating since the late 1960s and have recently attracted much attention as precursors for CVD of aluminum (W. L. Gladfelter et al., Chem. Mater. 1989, 1, 339). These tertiary amine alanes are less air-sensitive than the trialkylaluminums. Since there is no aluminum-carbon bonds in these compounds, carbon incorporation in the deposited films is minimized. A major problem for these complexes is their low thermal stability. Trimethylamine alane (TMAA) has been used as a precursor for CVD of aluminum and demonstrated high growth rates and low growth temperatures. Despite its high stability compared to other amine alane complexes, a disadvantage of TMAA as a practical CVD precursor is that it is a solid with a relatively high melting point. A few alane complexes with bulkier amines, such as triethylamine, diethylmethylamine and dimethylallylamine, are known to be liquids (J. K. Ruff et al., J. Am. Chem. Soc. 1960, 82, 2141). However, the thermal stability of tertiary amine alane complexes decreases as the amine gets bulkier.

Though dimethylethylamine alane (DMEAA) has been reported to be the optimal tertiary amine alane complex since it is a volatile liquid with considerable thermal stability (W. L. Gladfelter et al., U.S. Pat. No. 5,191,099), several problems still remain to be solved. DMEAA dissociates to give free amine, alane, and aluminum during storage as well as during vaporization processes. Excess amine is added to the precursor vessel to avoid the dissociation of the precursor during storage. However, this cannot solve the problems arising from the intrinsically poor vaporization behavior of DMEAA at elevated temperatures originating from its thermal instability. Aluminum particles have been reported to be observed in the gas phase during the CVD process using DMEAA (M. G. Simmonds et al., J. Vac. Sci. Technol. 1991, A9, 2782).

BRIEF SUMMARY OF THE INVENTION

The present invention describes amido alane precursors for chemical vapor deposition of aluminum, which are thermally stable at the temperatures at which the deposition reaction occurs, to solve the problems due to the instability of the tertiary amine alane complexes.

The object of the present invention is to provide volatile liquid or solid aluminum precursors which are capable of depositing high-quality aluminum for aluminum films as well as for films of composite materials containing aluminum under CVD conditions.

This and other objects of the invention can be achieved by amido amine alane complexes, $H_2Al\{(R^1)(R^2)NC_2H_4NR^3\}$, wherein $R^1$, $R^2$ and $R^3$ are each independently H or $C_1$–$C_3$ alkyl, which are non-pyrophoric and thermally stable in the gas phase at elevated temperatures. No thermal decomposition of these complexes was observed even at 220° C. The remarkably high thermal stability of these novel precursors according to the present invention is achieved by the bidentate amines which form intramolecularly coordinated amido amine alane complexes. As a result, the present invention makes the long-term storage and the gas phase delivery processes simpler and less troublesome than the conventional precursors. Most importantly, the present aluminum precursors do not dissociate to produce free alane or aluminum particles in the gas phase, which will affect the microstructures of the deposited films, so that they deposit aluminum films by the surface reactions only. Further objects and advantages of the invention will become apparent through reading the remainder of the specification.

DETAILED DESCRIPTION OF THE INVENTION

Figure 1:
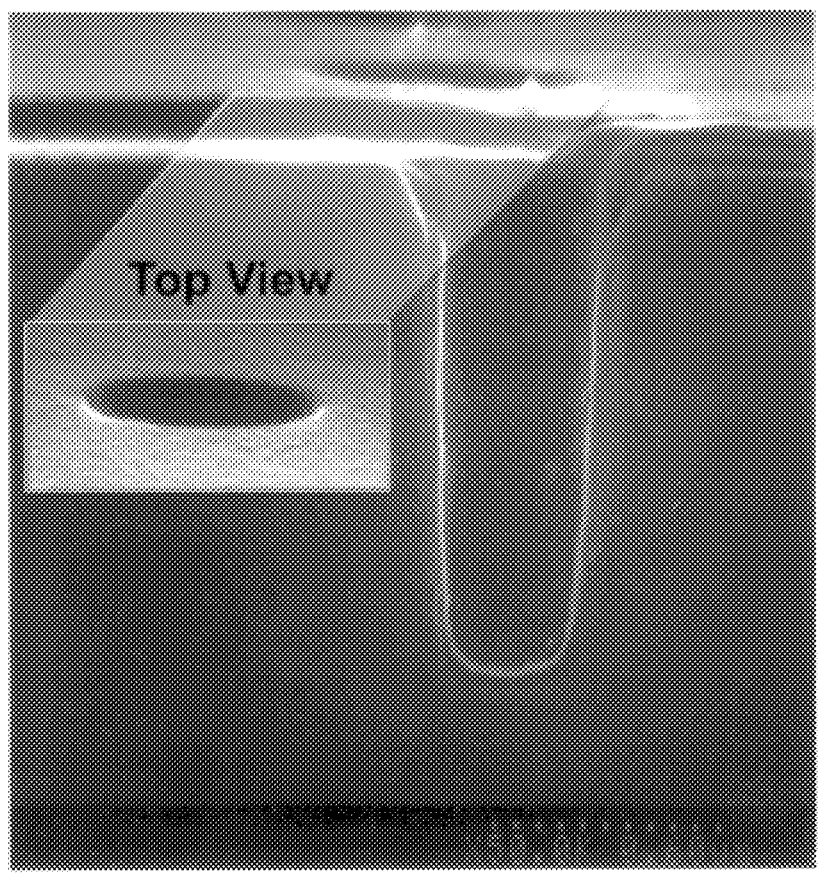
FIG. 1 is a scanning electron microscopy (SEM) image of an aluminum film deposited at 100° C. using DMEEDA as a precursor on a patterned TiN-coated Si substrate with high-aspect-ratio (>3.5) via holes of diameter of 0.3 $\mu$m. The inset shows a top view of a via highlighting smooth aluminum surface.

The present invention provides $H_2Al\{(R^1)(R^2)NC_2H_4NR^3\}$, wherein $R^1$, $R^2$ and $R^3$ are each independently H or $C_1$–$C_3$ alkyl, which are useful precursors for chemical vapor deposition (CVD) of aluminum. The precursors produce highly pure aluminum films in the presence or in the absence of hydrogen. The films thus formed are free from carbonaceous impurities since there is no direct bond between aluminum and carbon in the precursor molecules. The precursors are non-pyrophoric and thermally stable so that they maintain their molecular integrity in the gas phase at the temperatures at which the deposition reaction takes place.

According to the invention, $H_2Al\{(R^1)(R^2)NC_2H_4NR^3\}$ can be synthesized by the reaction of lithium aluminum hydride with $(R^1)(R^2)NC_2H_4N(H)R^3$.HCl as outlined in equation I.

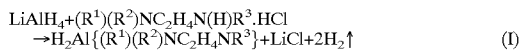

$$LiAlH_4 + (R^1)(R^2)NC_2H_4N(H)R^3 \cdot HCl$$
$$\rightarrow H_2Al\{(R^1)(R^2)NC_2H_4NR^3\} + LiCl + 2H_2\uparrow \qquad (I)$$

wherein $R^1$, $R^2$ and $R^3$ are each independently H, $CH_3$, $C_2H_5$ or $C_3H_7$.

These complexes are either distillable liquids or volatile solids. The vaporization behavior thereof at elevated temperatures was monitored up to 220° C. by gas phase infrared spectroscopy using a Perkin Elmer 1600 Series FT-IR spectrometer. The IR spectra showed no indication of free amines liberated from the precursors during the heating process. This indicates that they are thermally stable to maintain their molecular integrity in the gas phase at elevated temperatures. In other words, the aluminum precursors in the present invention are not pyrophoric and can be stored at room temperature.

The precursors obtained in the manner described above are subjected to a chemical vapor deposition apparatus comprising a precursor vessel, a Pyrex reactor and a vacuum system to produce aluminum thin films. The precursor vessel is maintained in the temperature range of 15°–70° C., preferably 20°–60° C. The precursor which has been vaporized is injected into the reactor with or without carrier gas. Carrier gas could be any inert gas. When the precursor reaches the substrate, it is thermally decomposed on the substrate. Silicon and TiN-coated-silicon wafers are used as substrates, but any substrates suitable for the CVD process may be used. Depositions are conducted in the temperature range of 60°–300° C. The reactor is maintained at 0.1 to 10 torr during the deposition reaction. However, pressures lower than $10^{-4}$ torr have been used successfully. The reaction pressure does not appear to be critical to the deposition of aluminum films. The deposition rate is dependent upon the reaction conditions used.

For the precursors to be useful it is essential that the amine is bound strongly enough to be vaporized without thermal decomposition, yet weakly enough to deposit aluminum on substrates at elevated temperatures. The present precursors deposit aluminum films at remarkably low temperatures, as low as 60° C., while they are thermally stable at elevated temperatures at which the deposition reaction occurs. The extremely high thermal stability of these precursors is realized by the bidentate amines which form intramolecularly coordinated alane complexes: one end of the diamine forms an amido bond to the metal center in an aluminum complex and the other fills the fourth coordination site of the metal. The ability of the present precursors to deposit aluminum films at low temperatures is especially important for processing multi-metal layer ICs to avoid thermally induced inter-diffusion of layer materials at interfaces. The low deposition temperatures exhibited by the present invention strongly suggest that the deposition of aluminum occurs via surface catalyzed reactions. In fact, these precursors deposit aluminum films selectively onto metallic or electrically conductive portions of a substrate surface while avoiding deposition on silicon dioxide or other non-conductive portions of the surface even at temperatures as high as 250° C. More interestingly, they selectively deposit aluminum on silicon versus hydrogen passivated silicon surfaces under ultra high vacuum conditions. The high selectivity with wide process window is another advantage of the present aluminum complexes as CVD precursors.

The deposited aluminum films using the present invention show very smooth surface morphology and good step coverage on patterned substrates with high-aspect-ratio via holes of sub-half micron size, and have no impurities such as carbon or nitrogen in the deposited films.

The aluminum precursors in the present invention can also be used to produce films of composite materials containing aluminum metal such as group III-V compound semiconductors as well as aluminum films.

The present invention will be illustrated in greater detail by way of following examples. The examples are presented for illustrative purpose only and should not be construed as limiting the invention, which is properly delineated in the claims.

All reactions and subsequent manipulations involving organometallic reagents were performed under argon or nitrogen atmosphere using Schlenk-type glassware and glove box techniques. All reagents were purchased from Aldrich Chemical Co. (Milwaukee, Wis.). All solvents were purchased from Baxter Healthcare Co. (Muskegon, Mich.) and freshly distilled from Na under nitrogen. The amines were freshly distilled under nitrogen. The amine .HCl adducts were prepared by mixing a diethyl ether solution of HCl with the corresponding free amine followed by filtration and drying in vacuum. Infrared spectra were recorded on either a BioRad FTS60A FT-IR spectrometer or a Perkin Elmer 1600 Series FT-IR spectrometer.

Example 1

Synthesis of $H_2Al(Me_2NC_2H_4NMe)$ (i.e., TMEDA)

In a glove box, $LiAlH_4$ (1.28 g, 33.7 mmol) and a magnetic stirring bar were transferred to a 100 ml three neck round bottom flask. A Schlenk tube containing 20 mmol of $Me_2NC_2H_4NHMe \cdot HCl$ (2.77 g, 20 mmol) was attached to the reaction flask. 50 ml of pentane was added to the flask and the resulting mixture was cooled to $-70°$ C. using a dry ice/acetone bath. $Me_2NC_2H_4NHMe \cdot HCl$ was added to the reaction mixture with constant stirring. The reaction mixture was slowly warmed to room temperature over 4 hrs and then stirred for 1 hr. The resulting reaction mixture was filtered through a medium porosity glass frit to remove the solids. The reaction flask was washed with pentane (2×5 ml) and the filtrates were collected. The solvent was removed in vacuo to get a white solid product. The crude product was recrystallized using pentane solvent. Melting point: 70° C., Sublimation temperature: 40°–45° C./0.08 torr.

Example 2

Synthesis of $H_2Al(Et_2NC_2H_4NEt)$ (i.e., TEEDA)

The above synthesis shown in Example 1 was repeated but substituting an equivalent quantity of $Et_2NC_2H_4NHEt \cdot HCl$ for $Me_2NC_2H_4NHMe \cdot HCl$. The product was isolated and recrystallized in pentane solvent as a white solid. Melting point: 70°–75° C., Sublimation temperature: 70°–75° C./0.3 torr.

Example 3

Synthesis of $H_2Al(Me_2NC_2H_4NEt)$ (i.e., DMEEDA)

The above synthesis shown in Example 1 was repeated but substituting an equivalent quantity of $Me_2NC_2H_4NHEt \cdot HCl$ for $Me_2NC_2H_4NHMe \cdot HCl$. The product was isolated as a colorless liquid. The liquid complex was purified by vacuum distillation. Boiling point: 39°–41° C./0.3 torr.

Example 4

Heat-treated TEEDA

TEEDA (7.21 g, 50 mmol) from Example 2 was transferred to a 25 ml Schlenk-type flask connected to a reflux condenser and heated at 150° C. for 30 min. The resulting solid was recrystallized using pentane solvent. Infrared spectra showed that no dissociation of free amine was occurring at temperatures as high as 220° C.

Example 5

Heat-treated DMEEDA

DMEEDA (8.61 g, 50 mmol) from Example 3 was transferred to a 25 ml Schlenk-type flask connected to a reflux condenser and heated at 150° C. for 30 min. The resulting liquid was distilled at 70°–80° C./0.03 mmHg. Infrared spectra showed that no dissociation of free amine was occurring at temperatures as high as 220° C.

Example 6

Chemical Vapor Deposition of Aluminum Films

Deposition was conducted in a glass reactor by feeding each precursor as prepared from Examples 1 to 3 with/ without argon as a carrier gas as described in Table 1. The temperature of the precursor vessel was maintained at 20°–60° C. A silicon wafer or a TiN-coated silicon wafer was used as a substrate. The substrate was heated to a temperature between 60° C. and 250° C. The total pressure of the system was maintained at 0.1 torr when no carrier gas was used. When argon gas was used as a carrier gas, the system was maintained at 3 torr.

TABLE 1

|  | Vessel Temperature, °C. | | Substrate |
| --- | --- | --- | --- |
|  | With Argon | Without Argon | Temperature, °C. |
| TMEDA[1] | 23 | 55 | 65–185 |
| TEEDA[2] | 23 | 55 | 93–204 |
| DMEEDA[3] | 23 | 35 | 80–250 |

[1] TMEDA = $H_2Al(Me_2NC_2H_4NMe)$
[2] TEEDA = $H_2Al(Et_2NC_2H_4NEt)$
[3] DMEEDA = $H_2Al(Me_2NC_2H_4NEt)$

Using the following conditions shown in Table 1, aluminum films were deposited on the wafers used. Auger spectra show no carbon and nitrogen impurities in the deposited films. Also, no deposition was observed on $SiO_2$ substrates which are non-conductive in the temperature range used above. This indicates that the aluminum precursors in the present invention are capable of carrying out selective CVD with a wide temperature range. Although the reactions were carried out mostly at the pressures of 0.1–3 torr, deposition of aluminum films was also observed at pressures lower than $10^{-4}$ torr. The aluminum films was observed by SEM to obtain the result of FIG. 1. FIG. 1 is a scanning electron microscopy (SEM) image of an aluminum film deposited at 100° C. using DMEEDA as a precursor on a patterned TiN-coated Si substrate with high-aspect-ratio (>3.5) via holes of diameter of 0.3 µm. Inset shows top view of a via highlighting smooth aluminum surface. SEM photos show good step coverage and surface morphology of the deposited aluminum films on high-aspect-ratio substrates.

I claim:

1. An amido/amine alane complex having the formula: $H_2Al\{(R^1)(^2)NC_2H_4NR^3\}$, wherein $R^1$ and $R^2$ are each independently $C_1$–$C_3$ alkyl and $R^3$ is H or $C_1$–$C_3$ alkyl, and their derivatives.

2. A complex in accordance with claim 1 wherein each $R^3$ is H.

3. A complex in accordance with claim 2 wherein each $R^1$ and $R^2$ is $CH_3$.

4. A complex in accordance with claim 1 wherein each $R^3$ is $CH_3$.

5. A complex in accordance with claim 4 wherein each $R^1$ and $R^2$ is $CH_3$.

6. A complex in accordance with claim 4 wherein each $R^1$ is $C_2H_5$.

7. A complex in accordance with claim 1 wherein each $R^3$ is $C_2H_5$.

8. A complex in accordance with claim 7 wherein each $R^1$ and $R^2$ is $CH_3$.

9. A complex in accordance with claim 7 wherein each $R^1$ is $C_2H_5$.

* * * * *